(12) United States Patent
Jääskeläinen

(10) Patent No.: US 6,819,419 B2
(45) Date of Patent: Nov. 16, 2004

(54) METHOD FOR ILLUMINATING PARTICLES CONTAINED IN A MEDIUM FOR OPTICAL ANALYSIS, AND OPTICAL PARTICLE ANALYSER

(75) Inventor: Juha Jääskeläinen, Helsinki (FI)

(73) Assignee: Janesko Oy, Vantaa (FI)

( * ) Notice: Subject to any disclaimer, the term of this patent is extended or adjusted under 35 U.S.C. 154(b) by 0 days.

(21) Appl. No.: 10/365,448

(22) Filed: Feb. 13, 2003

(65) Prior Publication Data

US 2003/0179374 A1 Sep. 25, 2003

(30) Foreign Application Priority Data

Feb. 13, 2002 (FI) .............................................. 20020289

(51) Int. Cl.$^7$ .............................................. G01N 15/02
(52) U.S. Cl. .................................................... 356/336
(58) Field of Search ................................ 356/335–343; 250/574

(56) References Cited

U.S. PATENT DOCUMENTS

| | | |
|---|---|---|
| 3,962,581 A | 6/1976 | Zimmerman |
| 3,975,084 A | 8/1976 | Block |
| 4,451,147 A | 5/1984 | Dobes et al. |
| 4,637,719 A * | 1/1987 | Herman ....................... 356/72 |
| 4,776,697 A | 10/1988 | Kamrat |
| 5,201,220 A * | 4/1993 | Mullins et al. .......... 73/152.42 |
| 5,434,411 A * | 7/1995 | Miyahara et al. ...... 250/339.07 |
| 6,141,097 A * | 10/2000 | Herman ...................... 356/335 |

* cited by examiner

Primary Examiner—Michael P. Stafira
(74) Attorney, Agent, or Firm—Burns, Doane, Swecker & Mathis, L.L.P.

(57) ABSTRACT

In a method for illuminating particles contained in a medium for optical analysis, and an optical particle analyzer, the medium is subjected to a light beam through a window which illuminates the particles to form an image of the particles. The window comprises a trapezoidal prism, a longer side surface of the parallel side surfaces of which forms a surface facing the medium. In the vicinity of the prism, the light beam is directed by a mirror surface and a cylindrical lens, which converts a shift of the light source to a change in the light beam angle.

19 Claims, 2 Drawing Sheets

METHOD FOR ILLUMINATING PARTICLES CONTAINED IN A MEDIUM FOR OPTICAL ANALYSIS, AND OPTICAL PARTICLE ANALYSER

This application claims priority under 35 U.S.C. §§ 119 and/or 365 to Patent Application Ser. No. 20020289 filed in Finland on Feb. 13, 2002, the entire content of which is hereby incorporated by reference.

CROSS-REFERENCE TO RELATED APPLICATIONS (NOT APPLICABLE)

STATEMENT REGARDING FEDERALLY SPONSORED RESEARCH OR DEVELOPMENT (NOT APPLICABLE)

INCORPORATION-BY-REFERENCE OF MATERIAL SUBMITTED ON A COMPACT DISC (NOT APPLICABLE)

BACKGROUND OF THE INVENTION (1) Field of the Invention

The invention relates to a method for illuminating particles contained in a medium for optical analysis, the medium being in contact with a window and subjected to a light beam that comes from a light source, through the window, and illuminates the particles to form an image of the particles; the window that is used being a trapezoidal prism a longer side surface of the parallel side surfaces of which forms a surface facing the medium; the light beam being modified to provide a beam of a predetermined thickness in the direction of the window normal; the light beam being directed to pass through one of the oblique surfaces of the prism serving as the window and to further travel inside the medium containing particles in the vicinity of the window surface making contact with the medium, substantially parallel to the surface, to thereby illuminate particles contained in a precisely predefined volume portion of the medium; and the image being formed by the light that is reflected back from the particles through the window. The invention also relates to a particle analyser.

The methods described above for illuminating particles, and analysers utilizing such methods are widely known in the industry. It is common in the industry today to transport or process material in the form of a particle suspension contained in a medium, such as a fluid. The particle referred to may be for example a crystal, fibre, grain, bubble, droplet, etc. The medium, in turn, may be water, or some other suitable, for example gaseous, substance.

Data about the amount of particles, their size distribution or shape is needed for monitoring and controlling different manufacturing processes. It is advantageous if such data can be brought into use timely and on a continuous basis. Therefore the best way to obtain the data would naturally be to receive it from an analyser that makes direct measurements from a process tube or container. This would ascertain that the measured sample provides an accurate picture of the process.

An optical measurement principle can be used to produce a particle analyser in which particles are illuminated and the light reflected by them is measured by an optical detector. The optical detector is selected according to the analysing task to be performed. The optical detector may thus be anything from a basic light cell to a multi-element image analyser. The reflected light can also be examined with the naked eye or by using suitable auxiliary optics. An essential aspect is that the particles to be illuminated are in a known, precisely defined volume portion of the medium. By restricting the illumination of the particles to a predetermined volume portion, a good contrast is obtained for the image received by the detector. As regards quantitative analysis, knowing the size of the fluid volume containing the illuminated particles provides a significant advantage.

(2) Description of Related Art Including Information Disclosed Under 37 CFR 1.97 and 1.98

One of the prior art solutions that can be mentioned is the crystal microscope, which is commonly used in sugar industry, one example of which is Jungner Crystal Projector, type KP3. This device has two windows between which the suspension to be measured travels. The windows form two parallel planes that are at an adjustable distance from one another. Particles, for example sugar crystals, are illuminated through one of the windows and an image of the particles is formed by means of a lens that is behind the other window. The image is projected in an enlarged form onto a matt-finished glass plate, thus enabling the personnel to examine the size and shape of the particles. The contrast is poor because the illuminated particles are visible against the light and therefore a precise automated electronic image analysis cannot be applied. It is not possible to draw quantitative conclusions either because the flow in the gap between the windows does not provide a correct picture of the main flow, i.e. the sample is not representative enough.

Another extremely wide group of prior art devices consists of what are known as photometers, which measure light absorption or reflection caused by particles. A typical example of a photometer that can be mentioned is the device described in U.S. Pat. No. 3,962,581. A characteristic of a photometer-type device is that the illumination is provided by a cone of rays passing relatively perpendicularly through a process window. A disadvantage is that the borders of the illuminated volume portion are not precisely marked and therefore the device is only applicable in quantitative determining based on an adjustment curve. The adjustment curve must always be experimentally defined for each application separately.

To eliminate the shortcomings in the solutions of the prior art described above, a method for illuminating particles for optical analysis and an optical particle analyser were developed in the past, the analyser being described in the following patent publications: FI 77330 (U.S. Pat. No. 4,776,697; JP 1,681,781; DE 3,700,286). A shortcoming of this prior art solution involves the changing of the angle of the light beam used in the illumination. Because the device is to be used for measuring particles in different media having different refractive indexes, the angle of the light beam used in the illumination must be changed according to the refractive index concerned. The adjustment of the illumination angle need not take place on a continuous basis, but it must be possible to set the angle application-specifically, i.e. whenever the refractive index of the medium to be measured changes. Another disadvantage is that the angle formed by the direction from which the particles are viewed and the direction of the illumination is great and therefore the analyser easily becomes impractical in terms of size and shape. These disadvantages are not discussed in any way in the Finnish Patent Publication, i.e. the publication does not even put forward any suggestions as to how to solve these problems.

BRIEF SUMMARY OF THE INVENTION

It is an object of the present invention to provide a method and an optical particle analyser that allow the shortcomings of the prior art to be eliminated. This is achieved by the invention. The method of the invention is characterized in that the light beam coming from the light source is directed to pass in the vicinity of the prism serving as the window through a mirror surface and a cylindrical lens, which direct the light beam to the prism and convert a shift of the light source to a change in the light beam angle. The optical particle analyser of the invention, in turn, is characterized in that the particle analyser comprises a mirror surface and a cylindrical lens placed in the vicinity of a prism serving as the window, the surface and lens being configured to direct a light beam coming from a light source to the prism and convert a shift of the light source to a change in the light beam angle.

One of the major advantages of the invention is that the light beam angle used in the illumination can be changed in a very simple manner according to the refractive index of the medium. A further advantage is that when seen from the light source, the particles are viewed and illuminated from the same direction and thus the analyser can be made practical in terms of size and shape. Still another advantage of the invention is that it is simple and therefore economical to implement.

BRIEF DESCRIPTION OF THE SEVERAL VIEWS OF THE DRAWINGS

In the following, the invention will be described in greater detail with reference to a preferred embodiment illustrated in the accompanying drawings, in which.

DETAILED DESCRIPTION OF THE INVENTION

Figure 1:
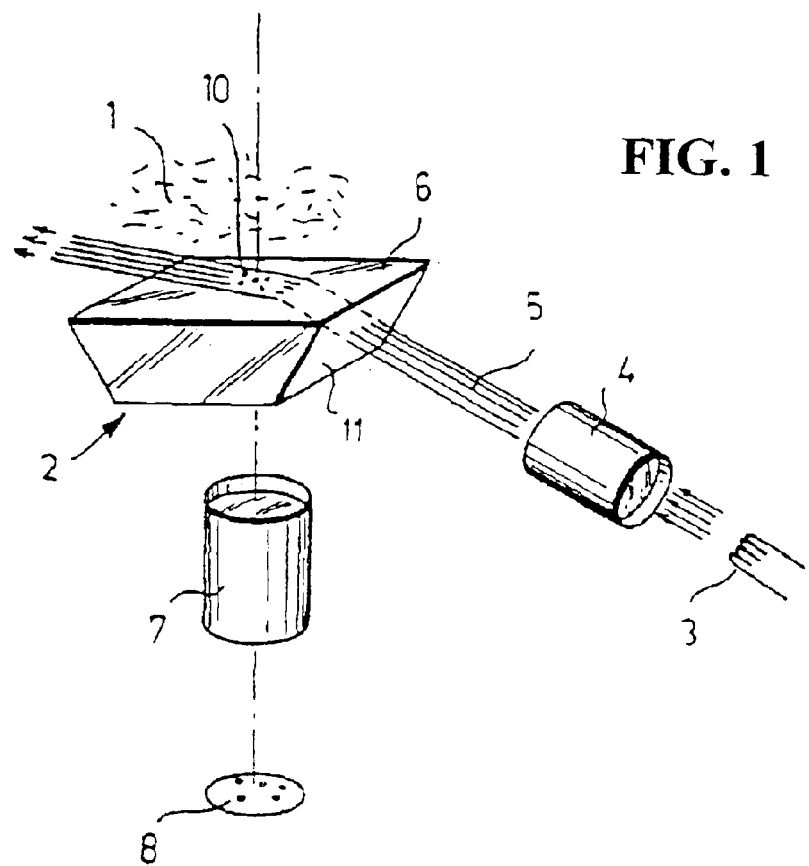
FIG. 1 is a schematic view of a basic principle applied to the method and apparatus of the invention.

FIG. 1 shows a schematic view of a basic principle of the invention. A particle suspension flow 1 consisting of a medium to be measured and of particles contained in the medium is separated from an optical system by means of a window 2. As a result, the particle suspension in FIG. 1 flows above the upper surface of the window 2, the upper surface of the window 2 thus making contact with the particle suspension.

Reference numeral 3 in FIG. 1 denotes a light source. A beam of light coming from the light source 3 is modified in the direction of the window normal to provide a band-like beam 5 of a precisely predetermined thickness by using condenser optics 4, for example. The band-like light beam is directed to travel inside the medium containing particles in the vicinity of the surface 6 at the interface between the window 2 and the medium, i.e. the suspension containing particles, substantially parallel to the surface 6. In this context the expression "substantially parallel to" means that the angle between the band-like beam 5 and the surface 6 is small. In addition, the beam and the surface are close to each other.

Figure 2:
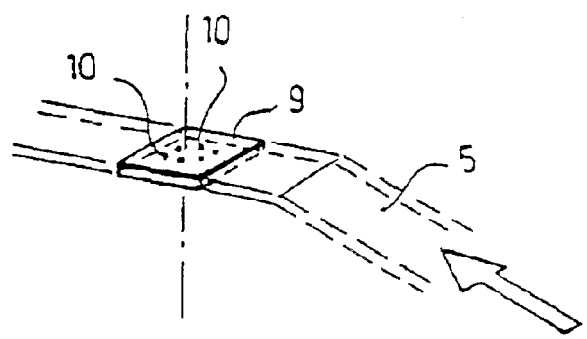
FIG. 2 is a schematic view of a precisely defined volume portion utilized in the basic principle of the invention.

The light beam 5 of a precisely predetermined thickness that travels close to the surface 6 and substantially parallel to it is then used for illuminating particles 10 contained in a precisely predefined volume portion 9 of the medium flow. This precisely defined volume portion 9 is shown in FIG. 2. The illuminated particles 10, in turn, are shown schematically in FIGS. 1 and 2. An arrow in FIG. 2 shows the direction of travel of the light beam 5.

An image of the particles 10 illuminated as described above is projected through an object lens system 7, whereby an image 8 is formed to an image plane and can be examined with the naked eye or modified into a message by means of a detector.

The window may be formed of a trapezoidal prism, for example. In the example of FIG. 1, the prism is placed such that the longer surface of its parallel side surfaces faces the medium. The band-like light beam 5 is directed to pass through one of the oblique surfaces 11 of the prism. Since the material of the prism is optically denser than the medium, the beam diverts away from the surface normal. The illuminated volume portion 9 is adjusted in the direction of the surface normal by providing the condenser optics 4 with restrictors that restrict the thickness of the beam 5 precisely to a desired value. On the surface 6 level the volume portion 9 can be restricted using a restrictor of the field of view of the lens 7, for example.

The above disclosure relates to the basic technology underlying the method and optical particle analyser of the invention. The above aspects have also been disclosed in the FI Patent 77330 mentioned earlier.

As already stated, if the above described basic principle is to be used in measurements in which particles are measured in different media having different refractive indexes, the angle of the light beam 5 to be used in the illumination, i.e. the angle at which the light beam meets the prism serving as the window 2, must be changed according the refractive index of each particular medium. The adjustment of the illumination angle does not need to be a continuous operation, but it must be possible to set the angle application-specifically, depending on the medium. A problem in the above basic principle is that up to now it has not been possible to change the angle of the light beam in an advantageous manner. It has also been observed that the angle formed by the direction from which the particles are viewed and the direction of the illumination is great. This becomes apparent from FIG. 1. Consequently, it has been difficult to implement an analyser employing the disclosed basic principle that would be practical in terms of size and shape.

Figure 3:
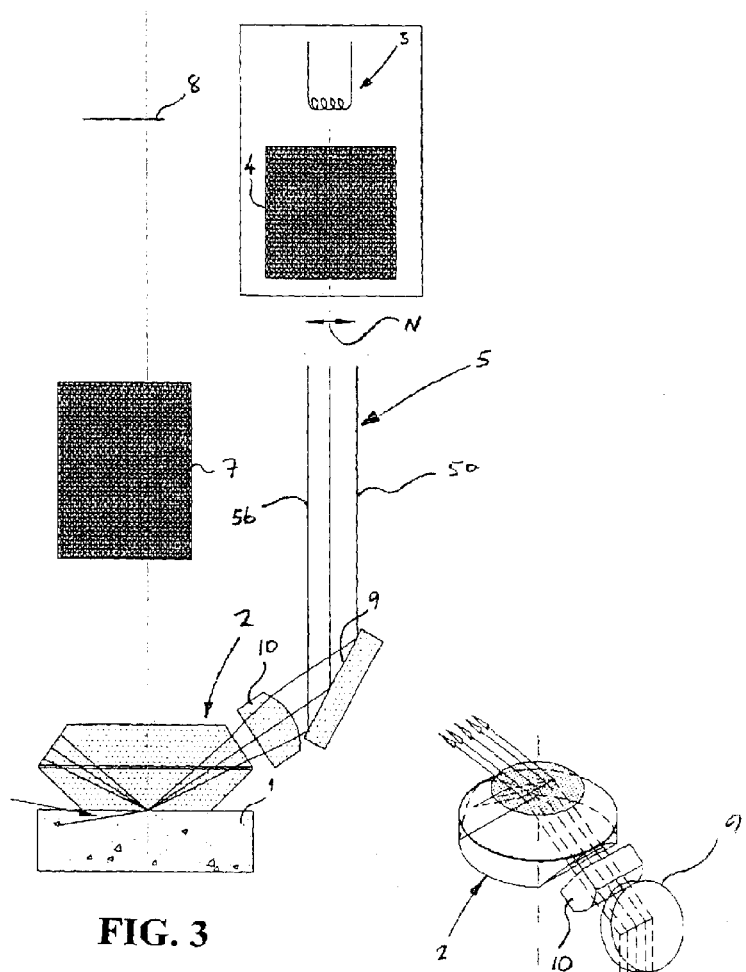
FIG. 3 is a schematic side view of an optical particle analyser of the invention.
Figure 4:
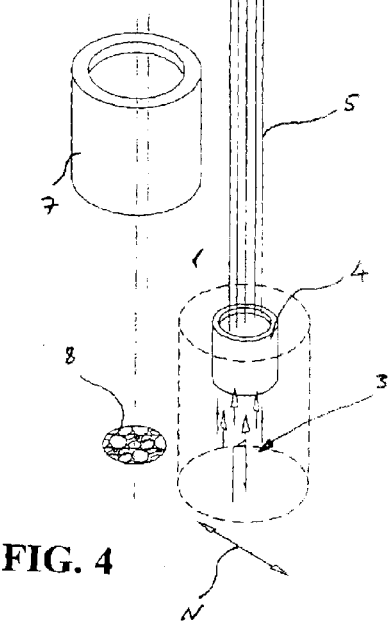
FIG. 4 is a schematic perspective view of the optical analyser of the invention.

FIGS. 3 and 4 are schematic views of an embodiment of the invention. Like parts are indicated with like reference numerals in FIGS. 3 and 4 and in FIGS. 1 and 2.

In the example shown in FIGS. 3 and 4 the light beam 5 coming from the light source 3 is directed according to the basic idea of the invention to pass in the vicinity of the prism serving as the window 2 through a mirror surface 9 to a cylindrical lens 10. The cylindrical lens 10 directs the light beam to the prism and converts a shift of the light source to a change in the light beam angle. It has been found particularly advantageous to shift the light source linearly and to convert the linear shift of the light source to a change in the light beam angle by means of the cylindrical lens 10. The linear shift of the light source is shown in FIGS. 3 and 4 by arrow N. The light source 3 may preferably be a laser diode.

In other words, the basic idea of the invention is that when seen from the light source, the directions of illumination and viewing are the same, the direction of illumination being only changed at the vicinity of the prism by means of the mirror surface 9. This allows an advantageous analyser to be obtained as regards its size and shape. The required change in the illumination angle depending on the refractive index of the medium can be obtained by directing the light beam to the cylindrical lens 10 after the mirror surface. This is illustrated particularly dearly in FIG. 3. The cylindrical lens 10 thus allows different illumination angles to be provided by changing the place of the light source 3. This is illustrated in FIG. 3, where a light beam marked with reference numeral 50 represents a beam used for a medium of a low refractive index. If the refractive index of the medium is high, the light source 3 is shifted as shown by arrow N so that the light beam travels as shown by the beam marked with reference numeral 56 in the Figure.

The above mentioned cylindrical lens 10 is used in the invention also for focusing the light beams from different angles to a specific point on the surface 6. The light beams are preferably focused to the same point because then the position of the object lens system 7 does not need to be changed in connection with a change of angle. In the case of a symmetrical prism it is particularly advantageous to focus the light beams to the centre of the prism.

In this context the term 'cylindrical lens' is not to be understood as a restricting definition but it should be given a broader interpretation. The idea is that the term also covers different lens systems consisting of a plural number of lenses etc. The invention can also be implemented with the mirror surface and the cylindrical lens arranged in a reverse order than in the example of FIGS. 3 and 4, i.e. the change of angle is made before the mirror surface. The structure according to FIGS. 3 and 4, however, allows smaller components to be used.

The prism serving as the window 2 can be advantageously formed such that the light reflected from the interface between the prism and the medium exits the prism through a polished surface on the opposite side thereof. The prism can be advantageously sealed against a conical surface.

The embodiment of the invention disclosed above is in no way meant to restrict the invention, but the invention can be entirely freely modified within the scope of the claims. It is therefore apparent that the optical analyser of the invention or its details do not necessarily need to be exactly as shown in the Figures, but other solutions are also possible.

What is claimed is:

1. A method for illuminating particles contained in a medium for optical analysis, the medium being in contact with a window and subjected to a light beam that comes from a light source, through the window, and illuminates the particles to form an image of the particles; the window that is used comprising a trapezoidal prism, a longer side surface of the parallel side surfaces of which forms a surface facing the medium; the light beam being modified to provide a beam of a predetermined thickness in the direction of the window normal; the light beam being directed to pass through one of the oblique surfaces of the prism and to further travel inside the medium containing particles in the vicinity of the window surface making contact with the medium, substantially parallel to the surface, to thereby illuminate particles contained in a precisely predefined volume portion of the medium; and the image being formed by the light that is reflected back from the particles through the window, the method comprising: directing the light beam coming from the light source to pass in the vicinity of the prism with a mirror surface and a cylindrical lens, which direct the light beam to the prism and convert a shift of the light source to a change in the light beam angle.

2. A method according to claim 1, wherein a linear shift of the light source is converted to a change of angle in the light beam by the cylindrical lens.

3. A method according to claim 1, wherein light beams from different angles are focused to a common point on the prism by the cylindrical lens.

4. A method according to claim 1, wherein the light beam is directed through the mirror surface to the cylindrical lens.

5. An optical particle analyser comprising: a window comprising a trapezoidal prism, the window arranged to make contact with a medium containing particles to be analysed, a longer surface of the parallel side surfaces of the prism being arranged to form a surface facing the medium; a light source configured to illuminate the particles through the window; a lens system configured to form an optical image of the illuminated particles, and an optical means configured to modify a light beam coming from the light source to provide a band-like beam of a precisely predefined thickness, the light beam being arranged to be directed to pass through one of the oblique surfaces of the prism and to further travel inside the medium containing particles in the vicinity of the window surface making contact with the medium, substantially parallel to the surface, the lens system being configured to collect the light reflected back through the window from the particles contained in a precisely predefined volume portion of the medium flow and illuminated by the band-like light beam for the purpose of forming an optical image, the particle analyser further comprising: a mirror surface and a cylindrical lens placed close to the prism, which are configured to direct the light beam coming from the light source to the prism and to convert a shift of the light source to a change in the light beam angle.

6. A particle analyser according to claim 5, characterized in that a linear shift of the light source is arranged to be converted to a change in the light beam angle by the cylindrical lens.

7. A particle analyser according to claim 5, characterized in that light beams from different angles are arranged to be focused to the center of the prism by the cylindrical lens.

8. A particle analyser according to claim 5, characterized in that the mirror surface is configured to direct the light beam to the cylindrical lens.

9. A method according to claim 1, wherein the window further comprises a conical section, the prism being sealed against a surface of the conical section.

10. A method according to claim 9, wherein light beams from different angles are focused to a common point on the window by the cylindrical lens.

11. A particle analyser according to claim 5, wherein the window further comprises a conical section, the prism being sealed against a surface of the conical section.

12. A particle analyser according to claim 11, wherein light beams from different angles are focused to a common point on the window by the cylindrical lens.

13. An optical particle analyser comprising:

a trapezoidal prism having parallel side surfaces, one of the parallel side surfaces facing a medium containing particles to be analyzed;

a light source providing a light beam;

optical means for modifying the light beam of the light source to form a band with a predetermined thickness;

a mirror and a cylindrical lens provided between the optical means and the trapezoidal prism, the mirror and the cylindrical lens directing the modified light beam of the light source to an oblique surface of the trapezoidal prism, the mirror and the cylindrical lens converting a shift of the light source to a change in the light beam angle.

14. The optical particle analyser of claim 13, wherein a linear shift of the light source is converted to a change of angle in the light beam by the cylindrical lens.

15. The optical particle analyser of claim 14, wherein the light beam is directed by the mirror surface to the cylindrical lens.

16. The optical particle analyser of claim 15, wherein light beams before and after the linear shift of the light source are focused to a common point on the trapezoidal prism by the cylindrical lens.

17. The optical particle analyser of claim 15, wherein light beams before and after the linear shift of the light source are focused to the center of the trapezoidal prism by the cylindrical lens.

18. The optical particle analyser of claim 14, further comprising a conical section, the prism being sealed against a surface of the conical section.

19. The optical particle analyser of claim 18, wherein light beams before and after the linear shift of the light source are focused to a common point on the conical section by the cylindrical lens.

* * * * *